(12) United States Patent
Loh

(10) Patent No.: US 10,413,708 B2
(45) Date of Patent: Sep. 17, 2019

(54) SWIVEL ENHANCED GUIDEWIRE AND RELATED METHODS

(71) Applicant: Jeffrey Thomas Loh, Honolulu, HI (US)

(72) Inventor: Jeffrey Thomas Loh, Honolulu, HI (US)

( * ) Notice: Subject to any disclaimer, the term of this patent is extended or adjusted under 35 U.S.C. 154(b) by 258 days.

(21) Appl. No.: 15/402,501

(22) Filed: Jan. 10, 2017

(65) Prior Publication Data

US 2017/0189652 A1 Jul. 6, 2017

Related U.S. Application Data

(63) Continuation-in-part of application No. 14/452,449, filed on Aug. 5, 2014, now abandoned.

(30) Foreign Application Priority Data

Apr. 26, 2016 (EP) .................................... 16167171

(51) Int. Cl.
*A61M 25/09* (2006.01)
*A61F 2/46* (2006.01)
(Continued)

(52) U.S. Cl.
CPC ..... *A61M 25/09041* (2013.01); *A61F 2/4611* (2013.01); *A61M 25/09025* (2013.01); *A61F 2/44* (2013.01); *A61F 2/962* (2013.01); *A61F 2002/9511* (2013.01); *A61F 2002/9517* (2013.01); *A61M 2025/09116* (2013.01)

(58) Field of Classification Search
CPC ...... A61M 25/09025; A61M 25/09033; A61M 25/09016; A61M 25/09041; A61M 2025/09116; A61M 2025/09183; A61M 2025/09175; A61F 2/46; A61F 2/4601; A61F 2/4611; A61F 2/95; A61F 2/962; A61F 2/97; A61F 2002/9511; A61F 2002/9517
See application file for complete search history.

(56) References Cited

U.S. PATENT DOCUMENTS

| | | | | |
|---|---|---|---|---|
| 3,335,620 | A * | 8/1967 | Vertut ......................... | B25J 3/00 414/7 |
| 3,572,333 | A * | 3/1971 | Hubert .............. | A61M 25/0009 604/170.01 |

(Continued)

*Primary Examiner* — David J. McCrosky
(74) *Attorney, Agent, or Firm* — Richard Batt

(57) ABSTRACT

An elongate flexible steerable guidewire for facilitating placement of a medical implement is described having a proximal section, an intermediate section, and a distal steerable section. In embodiments the distal steerable section comprises a plurality of rotatable swivel members, and an elongate directional tip extending distally from the distal-most swivel member. At least one manipulation wire is secured to the swivel members and extends proximally to the proximal section. Axial movement of manipulation wires rotates the swivel members, thereby curving the guidewire and deflecting the directional tip. An actuator or handle may be incorporated with the guidewire. Methods include placing medical implements in target regions. Exemplary applications include guiding and placement of electrical leads in the spine, and placement of angioplasty devices in the vasculature.

17 Claims, 8 Drawing Sheets

(51) Int. Cl.
*A61F 2/95* (2013.01)
*A61F 2/962* (2013.01)
*A61F 2/44* (2006.01)

(56) References Cited

U.S. PATENT DOCUMENTS

| | | | | |
|---|---|---|---|---|
| 3,631,737 | A * | 1/1972 | Wells | B25J 9/06 |
| | | | | 414/737 |
| 4,259,876 | A * | 4/1981 | Belyanin | B25J 9/046 |
| | | | | 414/7 |
| 4,921,482 | A * | 5/1990 | Hammerslag | A61M 25/0144 |
| | | | | 600/585 |
| 5,480,382 | A * | 1/1996 | Hammerslag | A61M 25/0053 |
| | | | | 600/585 |
| 5,683,451 | A * | 11/1997 | Lenker | A61F 2/07 |
| | | | | 606/198 |
| 6,197,017 | B1 * | 3/2001 | Brock | B25J 3/04 |
| | | | | 414/5 |
| 7,682,319 | B2 * | 3/2010 | Martin | A61B 17/00234 |
| | | | | 600/139 |
| 8,137,339 | B2 * | 3/2012 | Jinno | A61B 17/062 |
| | | | | 474/148 |
| 8,298,161 | B2 * | 10/2012 | Vargas | A61M 25/00 |
| | | | | 600/587 |
| 9,629,738 | B2 * | 4/2017 | Kelly | A61F 2/07 |
| 2014/0039350 | A1 * | 2/2014 | Folk | A61M 25/09041 |
| | | | | 600/585 |
| 2016/0030120 | A1 * | 2/2016 | Yanagihara | A61B 1/0055 |
| | | | | 606/130 |

* cited by examiner

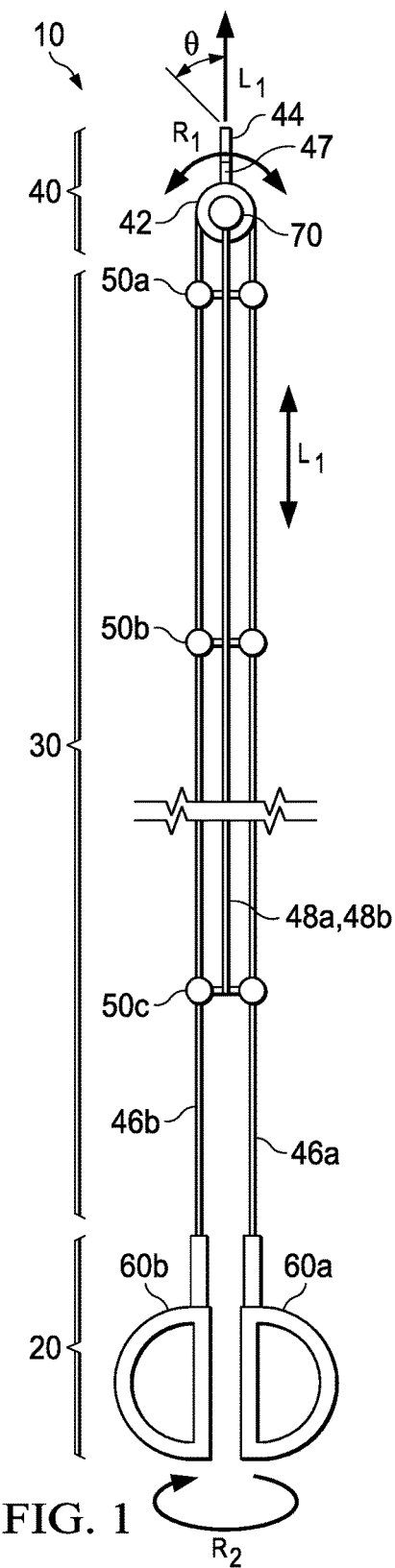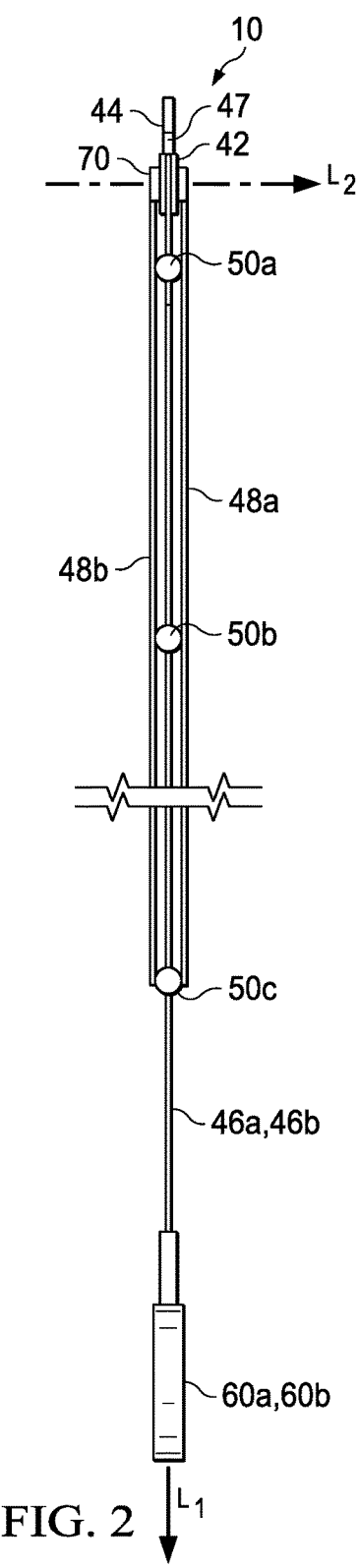
FIG. 1
FIG. 2

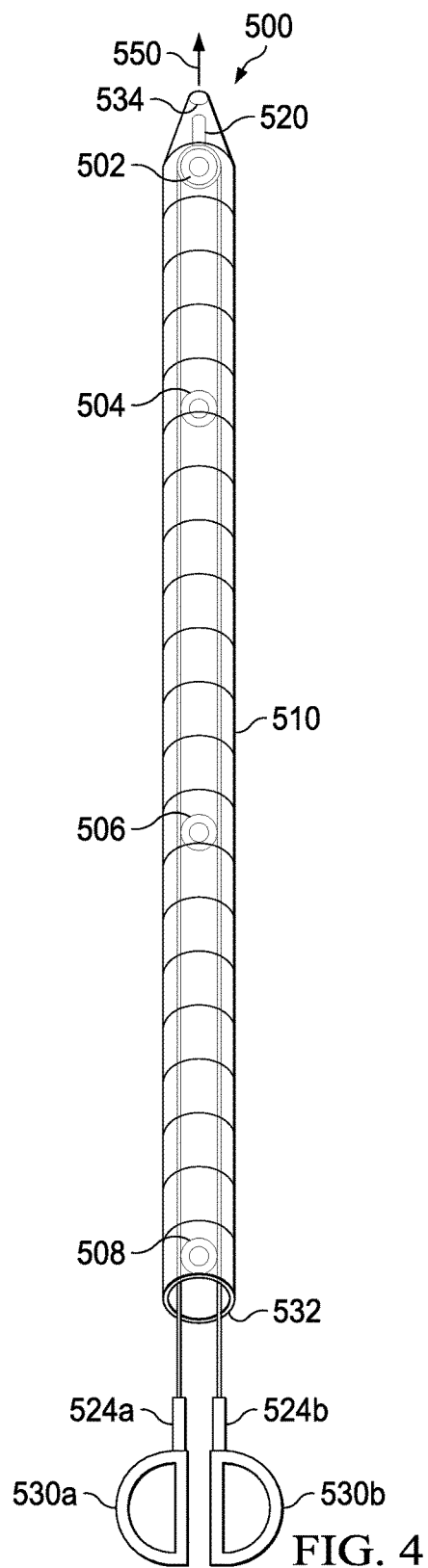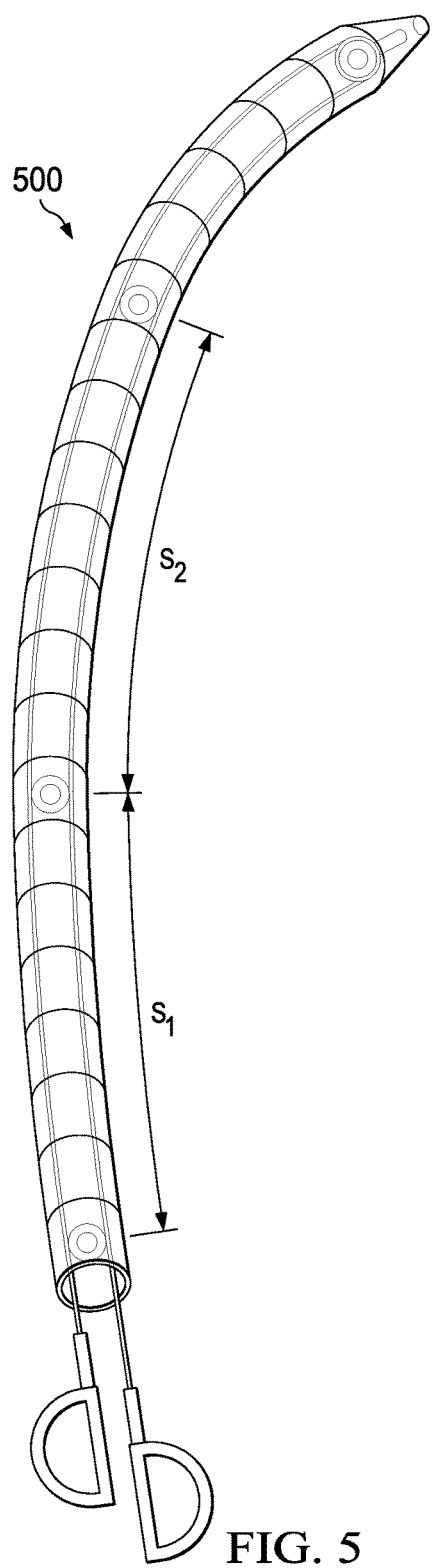

SWIVEL ENHANCED GUIDEWIRE AND RELATED METHODS

CROSS-REFERENCE TO RELATED APPLICATIONS

This application claims priority to EP Application No. 16167171.4, filed Apr. 26, 2016, entitled "Swivel Enhanced Guidewire"; and is a continuation in part application of U.S. non-provisional patent application Ser. No. 14/452,449, filed Aug. 5, 2014, entitled "Swivel Enhanced Guidewire and Related Methods"; both of which are incorporated by reference in their entirety.

BACKGROUND OF THE INVENTION

1. Field of the Invention

The present invention relates to a steerable guidewire and more particularly to a steerable guidewire having a swivel tip which may be precisely deflected. The guidewire is particularly suitable for use in conjunction with placement of a spinal cord stimulation lead in the epidural space of a patient, or alternatively, for the insertion of an endovascular product into a blood vessel of the patient.

2. Description of the Prior Art

The use of guidewires is well established to place catheters and other devices in target regions of the body. Generally, the guidewire is inserted into a vessel, and is navigated to a desired location. The catheter is fed over the guidewire and advanced through the vessel until the distal end of the catheter is positioned at a desired location. The guidewire is then retracted from the catheter and the catheter is left in the vessel to perform the endovascular intervention.

A guidewire may have a stiffness and flexibility along its length such that rotation or torque applied to the proximal section (e.g., to the hub) results in navigating the distal tip. Under fluoroscopy, a skilled practitioner can advance and torque the guidewire while observing its trajectory and location until a desired target region is reached. While this technique is generally acceptable, situations arise when even a skilled physician is not able to deflect the tip of the guidewire a sufficient degree to reach the target destination.

Various steerable guidewires have been described to provide controlled deflection and steering. Examples of steerable guidewires and devices are described in U.S. Pat. No. 7,481,778 to Cedro et al.; U.S. Pat. No. 7,449,002 to Wenstad; U.S. Pat. Nos. 4,815,478 and 4,813,434 both to Maurice Buchbinder et al.; U.S. Pat. No. 5,037,391 to Julius G. Hammerslag et al.; U.S. Pat. No. 5,203,772 to Gary R. Hammerslag et al.; U.S. Pat. No. 6,146,338 to Kenneth C. Gardeski et al.; U.S. Pat. No. 6,126,649 to Robert A. VanTassel et al.; U.S. Pat. No. 6,059,739 to James C. Baumann; U.S. Pat. Nos. 5,372,587 and 4,998,916 both to Julius G. Hammerslag et al.; U.S. Pat. No. 4,940,062 to Hilary J. Hampton et al.; U.S. Pat. No. 8,298,161 to Vargas; and U.S. Pat. No. 7,682,319 to Martin et al.

However, despite the above mentioned patents, there is still a need for a guidewire having more precise control and steering. There is still a need for a guidewire having a more complete range of motion, and that is reliable in each direction.

SUMMARY OF THE INVENTION

The description, objects and advantages of the present invention will become apparent from the detailed description to follow, together with the accompanying drawings.

A flexible steerable guidewire for facilitating placement of a medical implement includes an elongate body and a distal steerable tip section. The distal steerable section comprises at least one rotatable swivel member, and an elongate directional tip extending distally from the swivel member. At least one manipulation wire is secured to the swivel member and extends proximally to the proximal section. The manipulation wire is axially movably associated with the body such that axial movement of the manipulation wire rotates the swivel member, thereby deflecting the directional tip.

In embodiments, the guidewire further comprises a stabilization member extending proximally from the distal steerable section. The stabilization member is operably connected to the swivel member such that relative axial movement is prohibited between the swivel member and the stabilization member. In embodiments, the swivel member is movably connected to the stabilization member via a pin.

In embodiments, the guidewire further comprises at least one reinforcing strut disposed in the intermediate section. The reinforcing strut is secured to the stabilization member. In embodiments the reinforcing strut has a guide or eyelet through which the manipulation wire extends.

In embodiments, the directional tip is a wire member. In another embodiment, the directional tip has a length greater than the diameter of the swivel member.

In embodiments, the swivel member has a disc shape. In embodiments, body is open-framed.

In another embodiment, the guidewire further comprises a coating or an outer sheath surrounding the intermediate section. The sheath forms an atraumatic tip section covering the distal steerable section. The atraumatic tip section may comprise an ancillary port for a medical implement such as a second guidewire to pass there through. An ancillary channel extends from the ancillary port proximally.

In another embodiment, a guidewire assembly for facilitating placement of a medical device comprises a guidewire as recited in any one of the embodiments described herein, and an actuator operatively associated with the manipulation wires for applying longitudinally directed, push-pull forces to the wires so as to steer the directional tip of the guidewire assembly.

In embodiments, a multiple guidewire assembly for facilitating placement of a medical device comprises (a) a guidewire as recited in any one of the embodiments described herein, (b) an actuator operatively associated with the manipulation wire for applying longitudinally directed, push-pull forces to the manipulation wire for steering the directional tip of the guidewire assembly; (c) an outer sheath coaxially surrounding the intermediate section, and forming an atraumatic tip section covering the distal steerable section; and (d) an ancillary guidewire extending through an ancillary channel disposed in the sheath, and extending distally from tip section.

In embodiments, a method for placing a medical implement in a target region of a patient comprises the steps of: creating an entry through the skin of the patient; advancing a distal section of a guidewire into the entry; swiveling a directional tip of the guidewire, and continuing to advance the guidewire, until the target region is reached. A medical implement is then deployed in the target region. The guidewire is retracted from the patient such that the medical implement remains in the target region.

In embodiments, the step of deploying the medical implement in the target region comprises placing a lead. The step of placing the lead in the target region may comprise placing the lead in the epidural space of the patient.

In embodiments, the step of deploying the medical implement in the target region comprises placing an ancillary guidewire in the vasculature. The step of placing the guidewire in the vasculature may comprise placing the guidewire in a coronary vessel.

In embodiments, the swiveling step comprises rotating the directional tip about a lateral axis by axial manipulation of a push-pull wire and without compacting the guidewire.

In embodiments, the method further comprises rotating the directional tip about a longitudinal axis by rotating a proximal handle portion of the guidewire about the longitudinal axis.

In embodiments, the method further comprises re-inserting the guidewire into the medical implement subsequent to the step of retracting, and adjusting the location of the medical implement.

BRIEF DESCRIPTION OF THE DRAWINGS

FIG. 1 shows a front view of a guidewire assembly;

FIG. 2 shows a side view of the guidewire assembly shown in FIG. 1;

FIG. 4 shows a front view of another guidewire assembly in an unmanipulated state;

FIG. 5 shows the guidewire assembly shown in FIG. 4 in a manipulated state;

DETAILED DESCRIPTION OF THE INVENTION

Figure 3A:
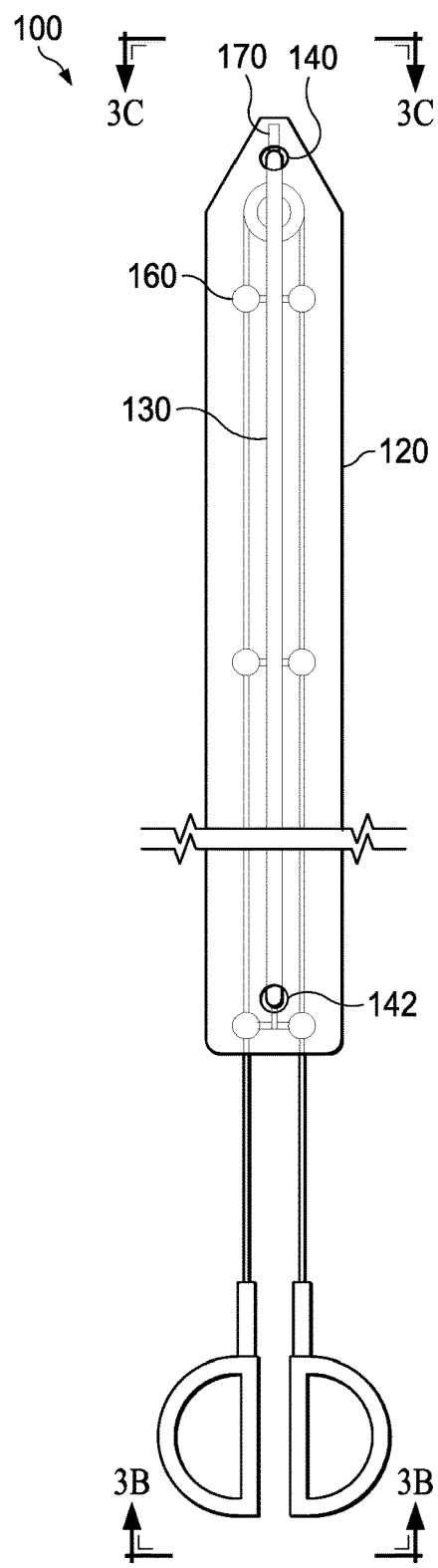
FIG. 3A shows a front view of a guidewire assembly having an exterior sheath.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

FIG. 1 illustrates a steerable guidewire 10 for deploying a medical implement (not shown). As discussed further herein, examples of medical implements include devices and implants such as a spinal cord stimulator lead.

Guidewire 10 is shown having an elongate open-framed body comprising a proximal section 20, intermediate section 30, and steerable distal section 40. A swivel member 42 is shown being rotatably mounted in the distal section. A directional wire or tip 44 protrudes from a superior aspect of swivel 42. Directional wire 44 is shown extending in an axial direction $L_1$.

Manipulating wires 46a, 46b are shown attached to opposite lateral points of swivel 42. Manipulating wires 46a, 46b extend from the swivel 42 proximally, through the intermediate section 30, and to the proximal section 20. Applying a push or pull force to the manipulating wires 46a, 46b at the proximal section moves the wires in the longitudinal direction $L_1$, causing the swivel or pulley to rotate $R_1$ about a lateral axis $L_2$ in the distal section.

FIG. 1 also illustrates finger holds or rings 60a, 60b for conveniently moving the manipulation wires 46a, 46b. The finger holds 60a, 60b are sized to each accommodate a single digit, and optionally, to allow the operator to manipulate wires simultaneously. It is to be understood, however, that other handles and actuators may be incorporated into the guidewire assembly to actuate the swivel, and steer or deflect the directional tip 44. An example of a control handle to allow for deflection of a catheter via first and second puller wires is described in U.S. Pat. No. 8,460,237 to Schultz.

As discussed above, the directional tip 44 may be deflected from the axis $L_1$ to steer the guidewire. The range of deflection (theta) of the directional tip may vary. In embodiments, the operator may manipulate the directional tip between 0 to 90 degrees from axis $L_1$. Additionally, the operator may rotate $R_2$ the guidewire as a whole about the longitudinal axis $L_1$ such that a full range of motion may be procured at the directional tip.

FIG. 1 also illustrates a plurality of struts (50a, 50b, and 50c) disposed along the guidewire length to maintain rigidity of guidewire, but still allow sufficient flexibility. The struts may comprise a rigid structure or frame and include spaces, eyelets or gaps to allow each manipulating wire 46a, 46b to freely pass through in the longitudinal direction $L_1$, yet prohibit substantial movement in the lateral direction ($L_2$).

Additionally, stabilization wires 48a, 48b are shown extending proximally from the swivel 42. The stabilization members are attached to reinforcing struts 50. Stabilization member also serves to anchor or support swivel 42. As shown, a pin 70 may be secured between distal ends of the stabilization wires 48a, 48b. The swivel or pulley may rotate about the pin. The stabilization members serve to ensure proper swivel position and action, as well as provide a static location for reinforcing struts.

Additionally, ensuring an axially static location for the swivel member is advantageous because the overall guidewire profile is prevented from being compacted, rigidized or shortened during actuation.

The guidewire may be formed of various biocompatible materials including steel, Nitinol, composites, and other metals and alloys typically used in the medical device industry. For example, the wire members such as the pull wires and stabilization wires may be formed of steel wire. The swivel, struts and handholds may be made of a metal or polymer materials. Adhesives, press fits, fasteners, and welding amongst other bonding techniques may be employed to join components.

The length of the guidewire may vary depending on the application. In embodiments, the intermediate section has a length ranging from 65 to 180 cm. The distal section has a length ranging from 5 to 10 mm.

The diameter of the guidewire may also vary depending on the application. In embodiments, the diameter of the guidewire at the intermediate section ranges from 0.01 to 0.05 inches, and more preferably from about 0.02 to 0.038 inches. And the diameter of the directional tip ranges from 0.01 to 0.03 inches, and more preferably from 0.014 to 0.02 inches.

Additionally, the diameter may vary along the length. The diameter of the distal section may be less than the diameter at the intermediate section. And the diameter along the intermediate section may decrease towards the distal section. In embodiments, a reduction in diameter is obtained by decreasing the size of the individual components such as the struts, or wires. Additionally, proximal sections may be increased in rigidity by adding material to the section. For instance, a coaxially positioned tube may be disposed in a proximal section to increase the rigidity in the proximal section.

Additionally, the directional tip is preferably atraumatic, and flexible. A suitable shape for the tip can be an elongate wire, a j-tip, a coil, or a combination thereof. Suitable materials for the tip member include Nitinol, metal alloys, and steel. Preferably, the structure affords a flexibility and stiffness such that when the swivel is rotated about the pin, directional tip may be deflected as intended to reach a desired target yet without excessive force to penetrate an anatomical wall or otherwise cause injury. The frame members may also be treated to reduce friction while preserving an open frame structure. In embodiments, thin coatings including for example lubricious polymers may be applied to reduce friction.

FIG. 2 is a side view of the guidewire shown in FIG. 1. As shown, the directional tip 44 is attached to the superior aspect of the swivel joint 42. Attached to the lateral aspects of the swivel joint on either side is a manipulating wire 46a, 46b. The manipulating wires course through a series of reinforcing struts. In embodiments, at least one stabilization wire is attached to each reinforcing strut, with the one stabilization wire attaching to each side of the fulcrum of the swivel joint. This distal attachment of stabilization wires to swivel joint fulcrum serves to secure the location of the fulcrum for swivel joint, which allows for the joint components to properly rotate.

The shape of the swivel or fulcrum member may vary. Examples of suitable shapes include without limitation: disc, arcuate, semi-circular, elliptical, sphere, cone, and triangular.

FIG. 2 also shows side profile of operator finger holds 60a, 60b, which allow for separate or simultaneous operation of each manipulating wire 46a, 46b.

FIG. 3A illustrates another steerable guidewire 100 differing from the open-framed guidewire 10 described above in connection with FIGS. 1-2 in that guidewire 100 includes an outer sheath or coating 120. In embodiments, the sheath 120 is a silicone or polymer based coating surrounding directional guidewire components. Without being bound to theory, the coating 120 is intended to provide additional structural stability to the guidewire, and to stabilize the manipulating wires, improving efficiency of directional tip 140. The coating 120 also is intended to help minimize frictional forces on the patient's tissue and intravascular blood components during operation.

FIG. 3A also shows a guidewire channel 130 extending through the polymer coating 120. The guidewire lumen commences at port opening 142, and terminates at port opening 140. The guidewire channel 130 may receive an accessory tool (not shown) such as a supplemental guidewire or delivery catheter. Channel 130 may also be used as a fluid transport lumen for delivery of dye contrast, a bioactive agent, or to evacuate a site.

In the case of advancing an ancillary guidewire through the guidewire channel, the ancillary guidewire can further help steer and ensure correct advancement of the complete guidewire assembly 100. For example, redundant steering may be carried out by a) turning or deflecting the direction tip by rotation of the swivel, b) advancing and steering the ancillary guidewire through the guidewire port 140, and c) further advancing the guidewire assembly over the ancillary guidewire. The steps may be repeated until a target region is reached.

In embodiments, once the target site is reached, the swivel-based guidewire assembly may be removed from the patient while leaving the ancillary guidewire in place. In embodiments, as described further herein, a medical implement may be advanced over the in situ ancillary guidewire to place the implant at the target site. By medical implements, it is meant to include without limitation catheters, stents, valves, embolic coils, filters, implants, fiducials, guidewires, leads, and other devices whether for surgical, therapeutic, or diagnostic purposes and regardless of whether implanted or removed from the patient.

Figure 3B:
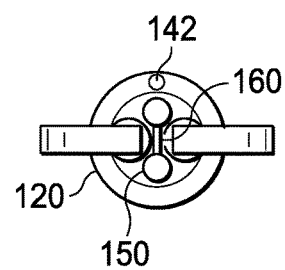
FIG. 3B shows a bottom view of the guidewire assembly shown in FIG. 3A.

FIG. 3B is a proximal end view of the coated guidewire 100 shown in FIG. 3A. As shown, the stabilization wires 150 are connected to reinforcing struts 160, to ensure stability and proper mechanics for directional tip 170. The polymer sheath or coating 120 surrounds internal metal components of directional guidewire. Better shown in FIG. 3B is the supplemental guidewire port 142, which allows an operator to advance an additional guidewire during surgical cases.

Figure 3C:
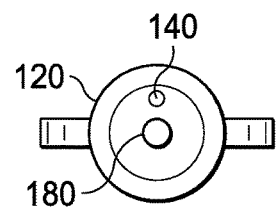
FIG. 3C shows a top view of the guidewire assembly shown in FIG. 3A.

FIG. 3C is a distal end view of the coated guidewire 100 shown in FIG. 3A. Better shown in FIG. 3C is the tapering of guidewire coating 120 to a smooth, rounded point 180, reducing frictional forces during advancement of the instrument. Distal opening 140 is shown in relatively close proximity to tip 180. The close proximity of the port 140 to point 180 facilitates tracking of the directional guidewire over the supplemental guidewire.

FIG. 4 shows another guidewire assembly 500 similar to the guidewire shown in FIGS. 3A-3C except that guidewire assembly 500 includes a plurality of swivel members 502, 504, 506, 508 disposed along the length of the guidewire body 510.

A directional wire or tip 520 protrudes from a superior aspect of swivel 502.

The catheter body 510 may incorporate an ancillary guidewire channel or passageway for accommodating the guidewire (not shown). Channel may commence at proximal port 532 and terminate at distal opening 534.

Manipulating wires 524a, 524b are shown extending longitudinally through the catheter body and attached to each of the swivel members 502, 504, 506, 508. Finger holds or rings 530a, 530b are shown at the proximal ends of manipulating wires for conveniently moving the manipulation wires. Applying a push or pull force to the manipulating wires at the proximal section moves the wires in the longitudinal direction, causing each of the swivels or pulleys to simultaneously rotate.

The handholds and swivel members shown in FIG. 4 operate in sync or registered such that de-acceleration or adverse transmission effects are avoided. Rotational forces are applied equally to each swivel.

It is also noteworthy that each swivel member is shown having an individual axis of rotation in a transverse direction to the longitudinal axis 550.

The axis of the swivels are fixed along the length of guide wire body such that manipulation of the finger holds, namely, steering the guidewire, cause the device to curve but not shrink in length. The catheter body may hold each swivel in position as described herein including, for example, by use of a pin means.

The presence of multiple swivel members enhances the structural integrity of the guidewire system. Another advantage of an elongate guidewire having multiple swivels along its length is that the entire guidewire may be curved and not merely the tip section. The structure shown in FIGS. 4-5 curves the entire catheter body as well as directs tip 520.

As discussed further herein, the swivel joints may each incorporate tracking markers (passive or active in nature) for facilitating guidance to a target site. Guidance systems including computer processors (and programmed with software) can evaluate the location of swivel tracking markers. The systems may be further configured to compute an amount of bend to the guidewire that is further required to guide the clinician to a target location.

FIG. 5 shows the guidewire assembly of FIG. 4 in a manipulated state. As shown, the presence of the swivels along the body results in the entire body curving when the manipulation wires are actuated.

Although swivels are shown along the entire catheter body in FIGS. 4-5, alternative arrangements include multiple swivels spaced along only a portion of the guidewire apparatus. For example, the swivels may be spaced along only the distal segment, or in some cases, along the intermediate and distal section.

Additionally, the number of swivel members may vary widely. Although four swivels are shown in FIG. 5, other arrangements within the invention include greater than four swivels, and in some cases, between 5 and 25 swivels, and more particularly between 1 and 15 swivels.

With reference to FIG. 5, the spacing ($S_1$, $S_2$, etc.) between swivel members desirably ranges from 0.5 to 1 cm. Additionally, different segments or sections of the guidewire may have different spacing between the swivels. For example, the spacing ($S_1$) in the proximal section may be greater than spacing ($S_2$) in the distal section, or visa versa.

APPLICATIONS

The guidewires described herein have various applications including for example, deployment of a spinal cord stimulator for the treatment of chronic pain. In one non-limiting exemplary procedure, one or more leads are introduced into the epidural space of the patient with the objective of positioning the electrodes near the spinal segment that innervates the targeted anatomical site.

Figure 6:
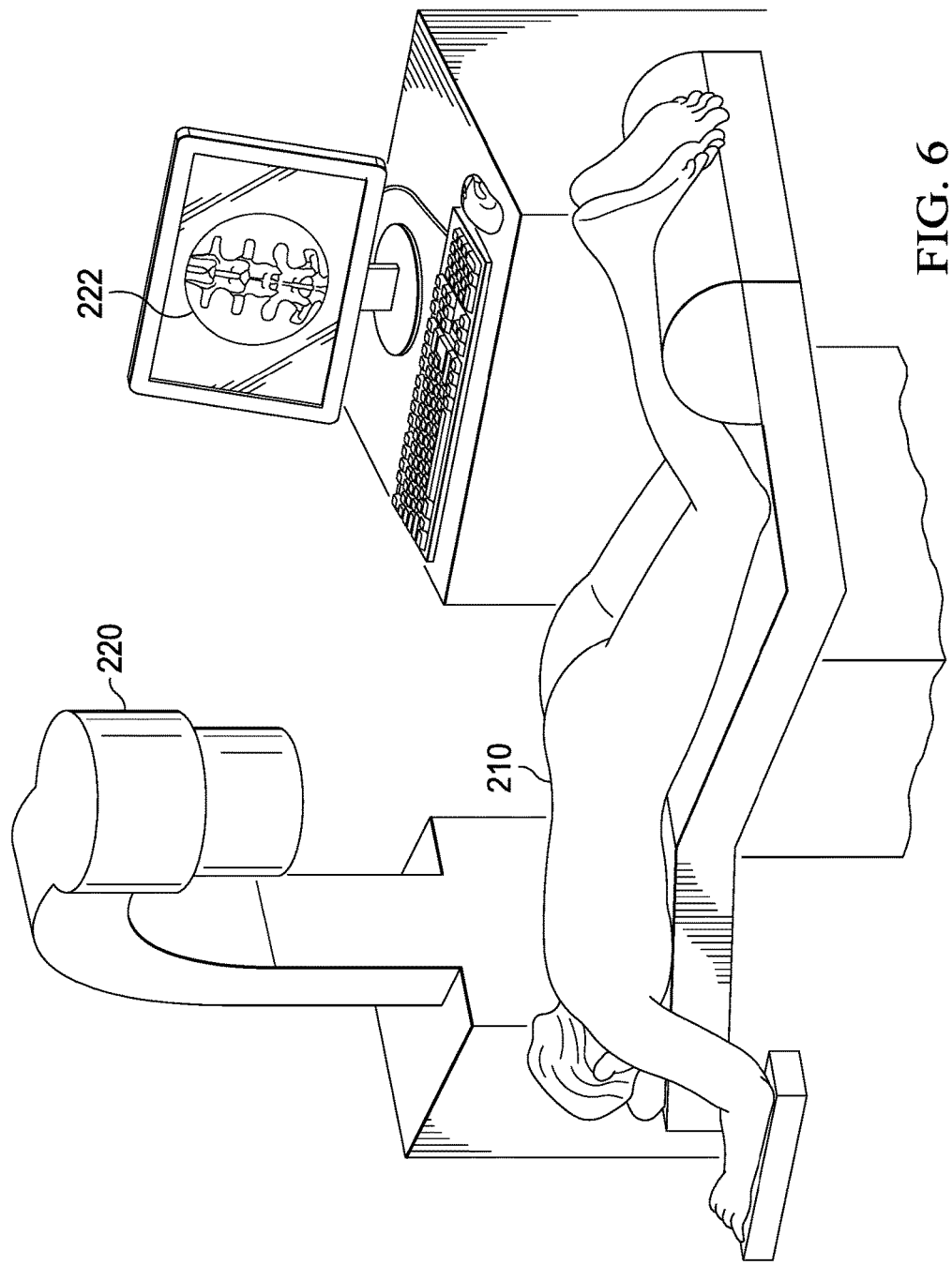
FIGS. 6-8 illustrate placement of a neurostimulation lead with a directional guidewire.
Figure 7:
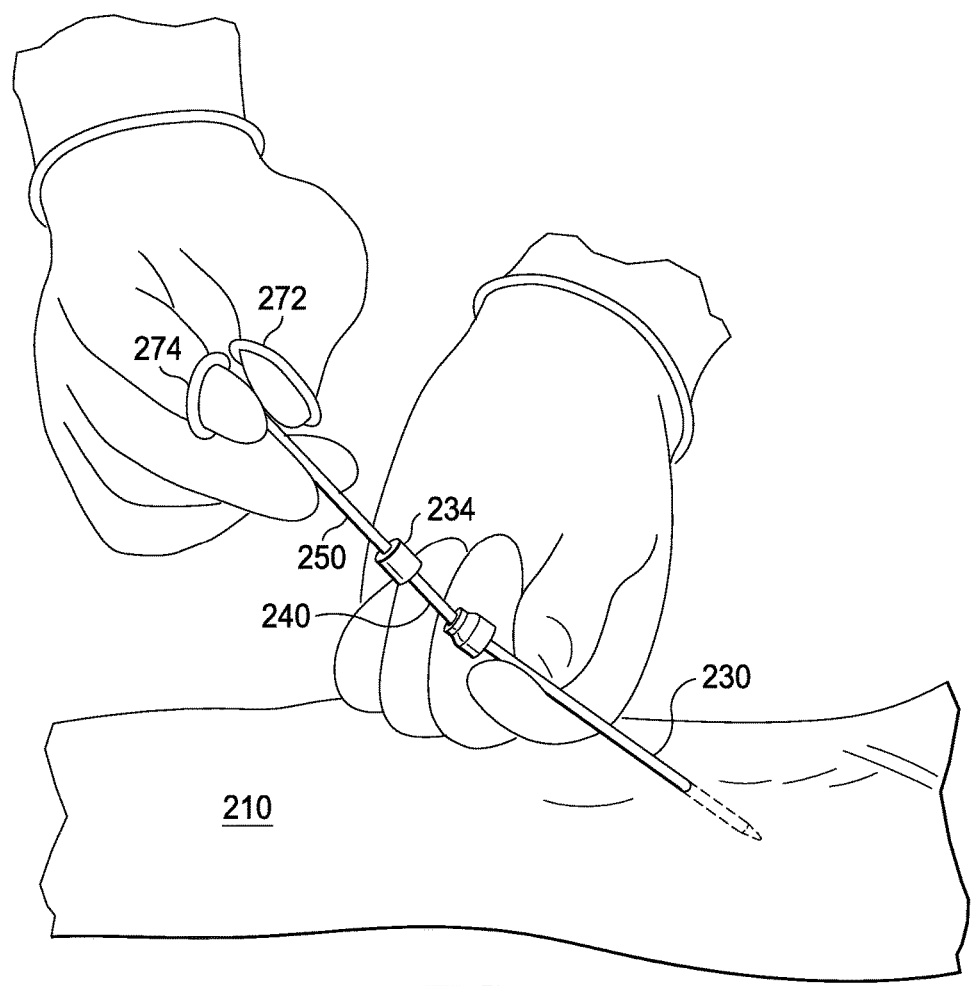
Figure 8:
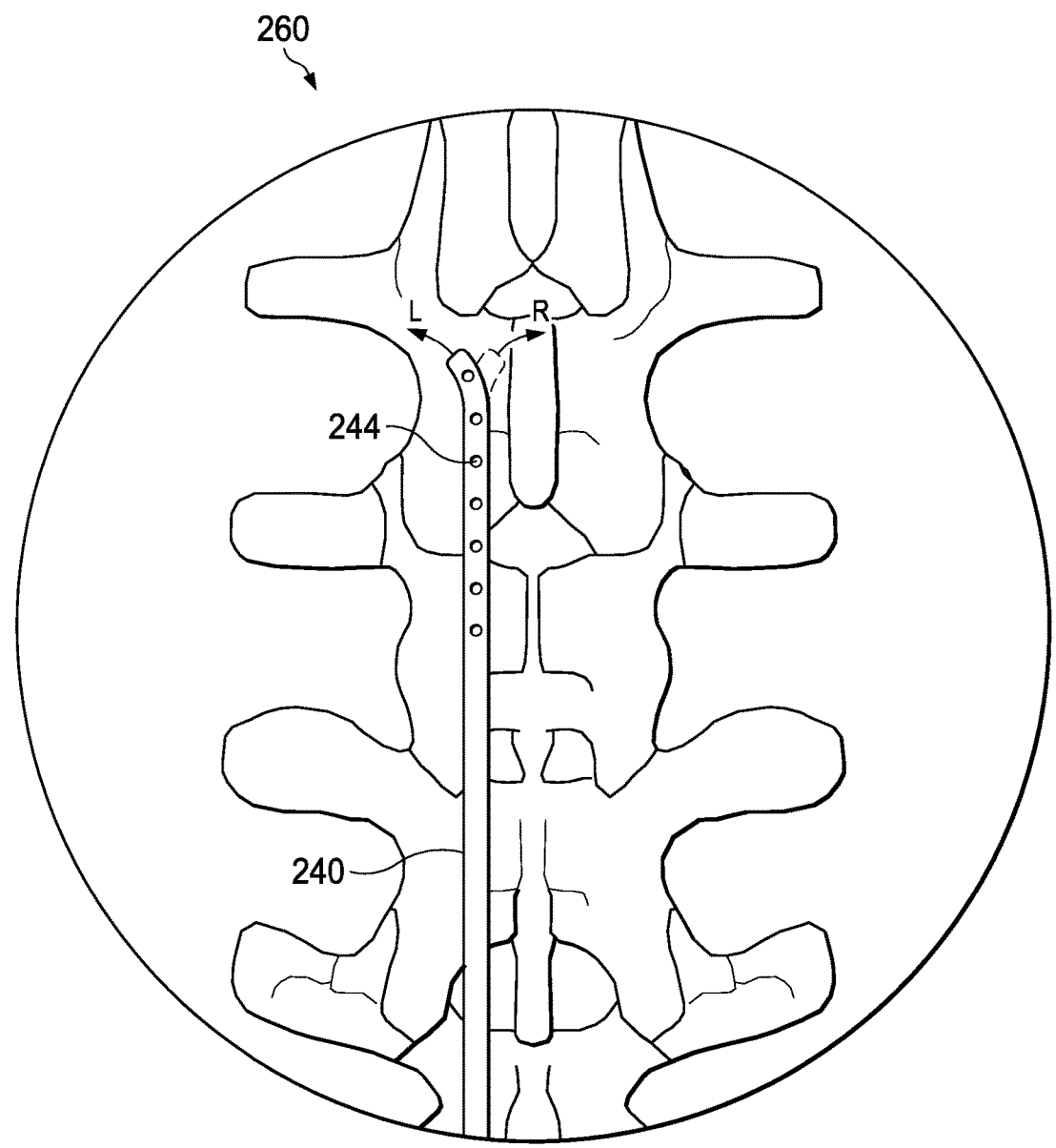

With reference to FIGS. 6-8, an exemplary spinal cord stimulation lead-placement procedure is described. First, a patient 210 is placed in a prone position with her back exposed. C-arm fluoroscope 220 is activated to provide live fluoroscopic images 222 of the target region.

After the patient is anesthetized, the epidural space is accessed utilizing an epidural needle 230 (e.g., a 14-gauge Tuohy needle). The spinal cord stimulator lead 240 is then inserted into the epidural space through the epidural needle 230.

With reference to FIG. 7, a guidewire 250 (e.g., a guidewire as described above in connection with FIGS. 1-3) is fed through stimulator lead hub 234 and through the shaft of the stimulator lead 240.

With reference to FIG. 8, by observing the live fluoroscopy image view 260, the operator advances the spinal cord stimulator lead 240, containing the directional guidewire 250, in the epidural space. To navigate the lead 240 directionally (e.g., to the right R or the left L), the operator will provide separate or concurrent opposing retraction and thrust on the separate finger holds 272, 274. As described herein, by actuating the finger holds, manipulating wires are longitudinally moved to deflect the directional tip. The operator may also achieve additional degrees of freedom motion by rotating the guidewire about the axial or longitudinal axis.

Once the directional tip angles in the operator's desired direction, the operator will advance lead 240 and directional wire assembly, so that the stimulator lead tracks in the correct direction. The operator may utilize multiple, fine changes in directional tip orientation while advancing the stimulator lead, until the stimulator lead overlies the desired area of the epidural space in the spine.

After lead position is achieved, the directional guidewire 250 is removed from the patient and the spinal cord stimulator lead will be trialed with the awakened patient to ensure the desired stimulus is obtained upon electrode 244 activation.

If the stimulator lead 240 is not in the correct location, the directional guidewire can be re-inserted into the spinal cord stimulator lead, and the lead will be repositioned to the proper location. If the stimulator lead is in an appropriate position, the lead will then be anchored to the patient for further patient care. An exemplary neurostimulation system is RestoreUltra® neurostimulation system, and the Titan™ anchor and 1×8 extension for each lead manufactured by Medtronic, Inc. (Minneapolis, Minn., USA). An exemplary stimulator lead is the Vectris® SureScan MRI Leads manufactured by Medtronic, Inc. (Minneapolis, Minn.).

In another embodiment of the present invention, the directional guidewire described herein is used in endovascular surgery, and in particular, to place a vascular device at a target site such as an arterial occlusion. Examples of vascular devices include but are not limited to stents, valves, angioplasty balloons, and artherectomy instruments.

In one embodiment, a method for placement of an endovascular device in a patient's occluded artery comprises first gaining arterial access at the level of the femoral artery.

Next, after arterial access is gained with hemodynamic control, a coated directional guidewire as described herein is introduced into the patient's arterial system. Examples of coated or sheathed directional guidewires are described above in connection with FIGS. 3-5.

Through the use of intravascular dye administration and fluoroscopy, the initial appearance of the patient's vasculature system will be delineated. The location of the patient's occluded artery will be confirmed at this time.

Next, using real-time fluoroscopy, the surgeon will manipulate the directional guidewire left, right, up and down to steer and advance the coated guidewire through the correct vascular pathway towards the target location. The ability of the directional guidewire to rotate up to 90 degrees or more from the midline provides the operator the ability to access arterial pathways with potentially difficult angles of access.

Figure 9:
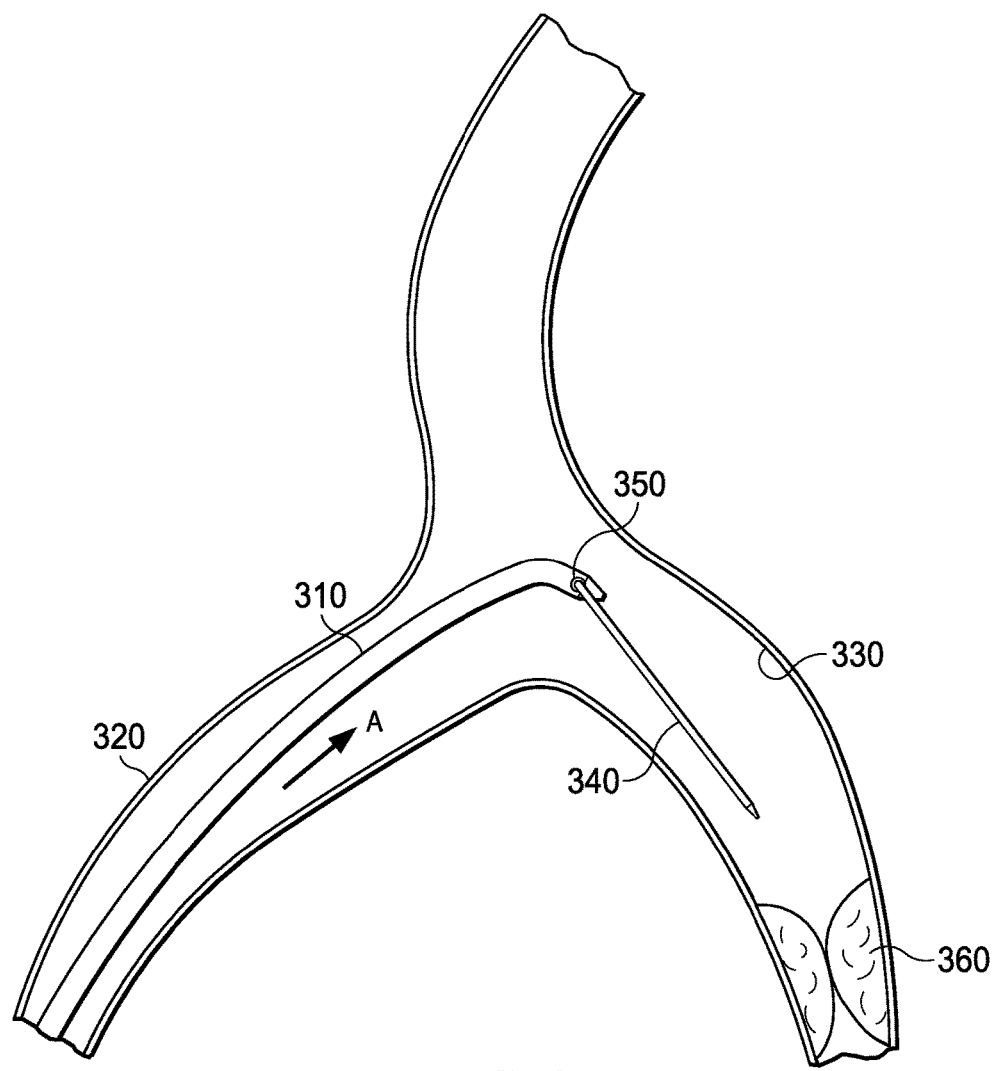
FIG. 9 illustrates advancement of a supplemental guidewire in a target vessel tract from a coated directional guidewire.

In another embodiment, and with reference to FIG. 9, in the event the directional guidewire 310 is directed at the proper vascular pathway 320 but fails to advance into the desired vascular track 330, a supplemental or ancillary guidewire 340 can be introduced through the accessory guidewire channel 350 in the sheath of the directional guidewire. With the tip of the directional guidewire pointing at the desired vascular tract, the supplemental guidewire 340 can then be advanced into the proper vascular tract 330. Once the supplemental guidewire has been inserted into the proper vascular tract, the directional guidewire can be advanced (A) over the supplemental guidewire to allow for advancement of the directional guidewire into the desired vascular pathway 330.

The directional guidewire will ultimately be advanced to the level of the surgical issue, at which time the supplemental guidewire 340 will be left at the surgical site 360, and the directional guidewire 310 will be removed. With the supplemental guidewire left in place, the surgeon can then advance a surgical stenting mechanism, balloon angioplasty device, or delivery catheter along the supplemental guidewire to properly place his surgical tool at the desired surgical site 360. A description of a balloon angioplasty and stent delivery system is described in, e.g., U.S. Pat. No. 5,639,274 to Fischell et al.

Once the surgical tool is in proper location, the supplemental guidewire 340 will be removed and the surgeon will employ the stenting device or angioplasty device to correct the patient's arterial occlusion 360.

Following correction of the patient's arterial occlusion, the surgeon will remove the surgical equipment from the patient's vasculature.

Completion of the surgical procedure will occur with closure of the femoral artery access site and proper achievement of hemostasis. The patient will then be awakened from anesthesia and transferred to the recovery room for post-operative monitoring.

Directional guidewire optionally includes at least one tracking element or means. Tracking means may be placed on the directional tip as shown in FIG. 1 (with reference to element 47) or incorporated into other components of the guidewire such as the swivel members 502, 504, 506, 508, or body 510 of the catheter shown in FIG. 4.

Tracking means can be passive or active-based. Examples of passive-based tracking means include radio opaque orientation marks such as non-symmetrical characters or symbols which are viewable under fluoroscopy. The 3D position may be computed from the real time fluoroscopic views showing the tracking element using well known mathematical algorithms and transformations.

Examples of active-based tracking elements include energy emitting or receiving components such as electromagnetic, infrared, and magnetic transmitters (transponders, receivers, etc.). The electromagnetic transmitters communicate with one or more position sensors disposed in the operating room (or on the fluoroscope itself) for tracking the 3D position of the transmitter(s).

Optionally, a plurality of position sensors (for example, 4 position sensors) are equally spaced on the edge of the image intensifier of the fluoroscope. The sensors are utilized to interpret the position of the directional guidewire. Because the relative spatial locations of the emitters on the directional guidewire are known a priori, the tracking sensors (in combination with a programmed computer) are able to locate the guidewire in three-dimensional space using well known mathematical transformations.

The directional guidewire (or other appliance) may be adapted with multiple transmitters in a pre-arranged orientation (e.g., linearly aligned) for enabling computation of the 3D location as well as trajectory or projection information. A trajectory path may be computed based on the geometry of the transmitters. For example, in the case of a directional guidewire incorporating a first proximal tracking element and second distal tracking element, a line may be computed, on a processor, extending form the proximal tracking element to the distal tracking element, and projecting thereon into the tissue. The physician may adjust the orientation of the tool to redirect the projection line (namely, the trajectory path) to the target in the patient.

The trajectory path may be overlaid onto the image output screen (e.g., a red trajectory line on monitor screen), allowing the operator to better plot a course of his surgical tool in relation to a patient's anatomy. Because the tracking and position sensors operate independently of the image intensifier and X-ray output source of the fluoroscope, changes in projected trajectory can be visualized independent of the use of real-time fluoroscopy, decreasing radiation exposure to the patient and allowing the surgeon to make better operative decisions.

Figure 10:
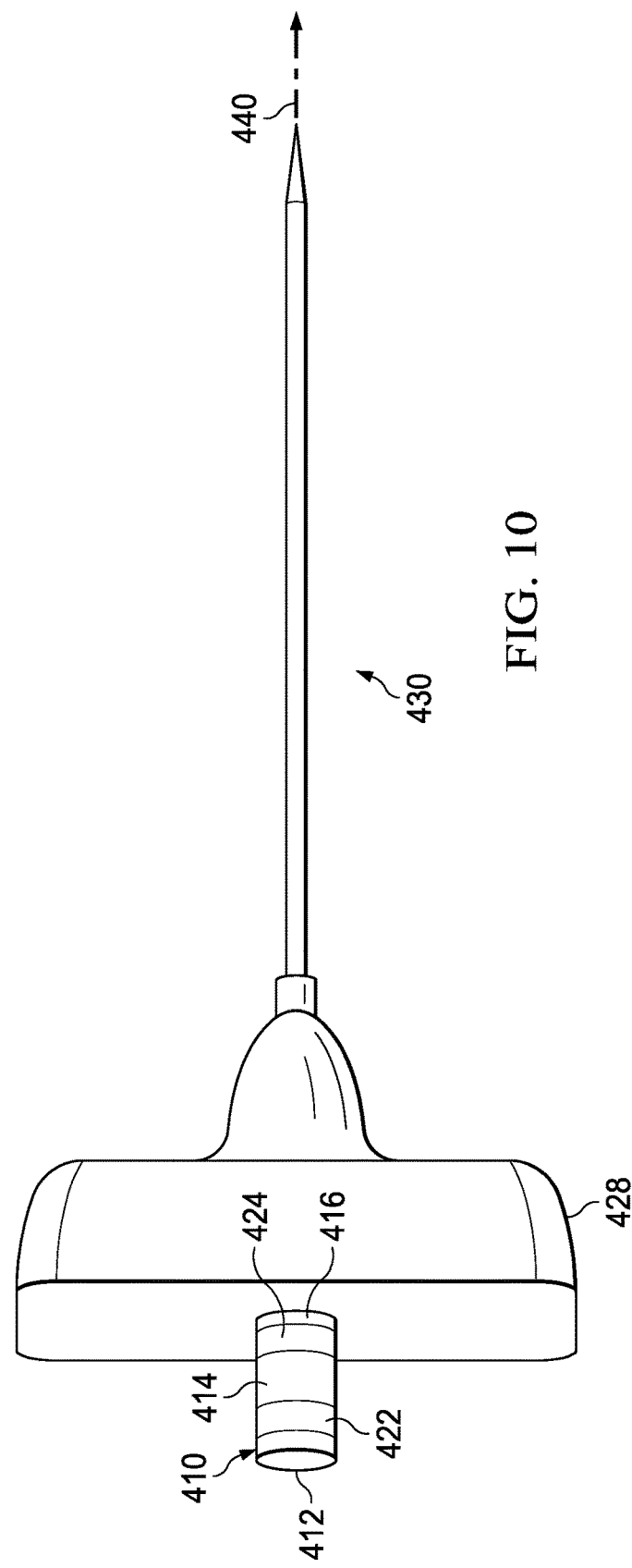
FIG. 10 shows tracking sensors incorporated onto a handle of a medical apparatus.

Optionally, and with reference to FIG. 10, a tracking probe 410 may be fastened to the medical implement or tool. Tracking probe is shown having a proximal end 412, a cylindrically shaped body 414, and a distal end 416.

A plurality of tracking elements 422,424 are incorporated into the body of the probe.

The probe is attachable to the proximal end of a handle 428 of the appliance 430. As discussed above, the tracking elements assist with navigation, guidance and trajectory 440 information during a procedure.

Although appliance 430 is shown as a bone access needle, the invention is not intended to be so limited. Probe may be mounted to other implements including without limitation fixation nails, guidewire instruments, catheters, etc. Probe may be provided as a stand alone accessory for mounting to various implements. Mounting may be carried out by adhesives, welds, and other fastening or connecting techniques as is known to those of skill in the art.

Additionally, the probes may be fastened to the medical implement at any location except where attachment would detract from the operation or safety of the medical implement. Preferably, but not necessarily, the probe is attached to the handle, shaft or tip.

Other modifications and variations can be made to the disclosed embodiments without departing from the subject invention. For example, in embodiments, the accessory guidewire port 350 may serve as a fluid delivery channel. In embodiments, the surgeon injects dye through the ancillary channel to provide focal contrast administration, further delineating the patient's vascular anatomy. The focal administration of contrast will help to potentially reduce the quantity of intravascular contrast utilized in a patient, reducing the risk of renal damage that can occur from large quantities of contrast dye administration.

I claim:

1. A flexible steerable guidewire for facilitating placement of a medical implement, the guidewire comprising:
    a proximal section, a flexible intermediate section, and a distal steerable section,
    a plurality of rotatable swivel members longitudinally disposed along the intermediate section and wherein the distal steerable section comprises a distalmost rotatable swivel member, and an elongate directional tip extending distally from the distalmost swivel member;
    a stabilization member extending proximally from the distal steerable section, and operably connected to the swivel members such that relative axial movement is prohibited between the swivel member and the stabilization member;
    at least one manipulation wire secured to the swivel members and extending proximally to the proximal section;
    wherein the at least one manipulation wire is axially movably disposed such that axial movement of the manipulation wire rotates the swivel members, thereby curving the flexible steerable guidewire and deflecting the directional tip; and
    an actuator operatively associated with the at least one manipulation wire for applying longitudinally directed, push-pull forces to said at least one manipulation wire for steering the directional tip of the guidewire assembly.

2. The guidewire of claim 1, further comprising at least one reinforcing strut disposed in the intermediate section, said reinforcing strut secured to the stabilization member.

3. The guidewire of claim 2, wherein the reinforcing strut further comprises a guide through which the at least one manipulation wire extends.

4. The guidewire of claim 1, wherein the directional tip is a wire.

5. The guidewire of claim 1, wherein each swivel member has a disc shape.

6. The guidewire of claim 5, wherein the directional tip has a length greater than the diameter of the swivel members, and ranges from 1-10 mm.

7. The guidewire of claim 1, wherein the swivel members are movably connected to the stabilization member via a pin.

8. The guidewire of claim 1, wherein at least the intermediate section is open-framed.

9. The guidewire of claim 1, further comprising an outer sheath, the sheath surrounding the intermediate section, and forming an atraumatic tip section covering the distal steerable section.

10. The guidewire of claim 9, wherein the atraumatic tip section comprises an ancillary port for a medical implement to pass there through.

11. The guidewire of claim 10, wherein the sheath further comprises an ancillary channel extending from the ancillary port proximally.

12. The guidewire of claim 1, further comprising a plurality of tracking transmitters.

13. The guidewire of claim 12 wherein the plurality of transmitters are linearly aligned.

14. The guidewire of claim 13 wherein the transmitters are located along the elongate directional tip.

15. The guidewire of claim 12 wherein each swivel member has one of the plurality of transmitters incorporated therein.

16. A guidewire assembly for facilitating placement of a medical device, the assembly comprising:
    a guidewire as recited in claim 1,
    a handle; and
    a tracking probe fastened to the proximal end of the handle wherein said tracking probe comprises a cylindrically shaped body and a plurality of tracking elements incorporated into the body of the tracking probe.

17. A multiple guidewire assembly for facilitating placement of a medical device, the assembly comprising:
    a guidewire as recited in claim 1,
    an actuator operatively associated with the at least one manipulation wire for applying longitudinally directed, push-pull forces to said at least one manipulation wire for steering the directional tip of the guidewire assembly;
    an outer sheath, the sheath coaxially surrounding the intermediate section, and forming an atraumatic tip section covering the distal steerable section and wherein the atraumatic tip section comprises an ancillary port for a medical implement to pass there through and an ancillary channel extending from the ancillary port proximally; and
    an ancillary guidewire extending through the ancillary channel, and distally from the ancillary port.

* * * * *